(12) United States Patent
Hacker et al.

(10) Patent No.: US 8,845,097 B2
(45) Date of Patent: Sep. 30, 2014

(54) OCT-BASED OPHTHALMOLOGICAL MEASURING SYSTEM

(75) Inventors: Martin Hacker, Jena (DE); Thomas Pabst, Stadtroda (DE); Ralf Ebersbach, Schmoelln (DE); Gerard Antkowiak, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 16 days.

(21) Appl. No.: 13/812,113

(22) PCT Filed: Jul. 2, 2011

(86) PCT No.: PCT/EP2011/003289
§ 371 (c)(1),
(2), (4) Date: Jan. 24, 2013

(87) PCT Pub. No.: WO2012/013283
PCT Pub. Date: Feb. 2, 2012

(65) Prior Publication Data
US 2013/0120711 A1    May 16, 2013

(30) Foreign Application Priority Data
Jul. 24, 2010    (DE) .................. 10 2010 032 138

(51) Int. Cl.
*A61B 3/14* (2006.01)
*A61B 3/10* (2006.01)
*A61B 3/00* (2006.01)

(52) U.S. Cl.
USPC ............................ 351/206; 351/205; 351/246

(58) Field of Classification Search
USPC ................................................. 351/200–246
See application file for complete search history.

(56) References Cited

U.S. PATENT DOCUMENTS 5,321,501 A    6/1994    Swanson et al.
5,999,302 A    12/1999    Sweeney et al.
(Continued)

FOREIGN PATENT DOCUMENTS

DE    10 2008 063 225 A1    7/2010
DE    10 2009 041 995 A1    3/2011
EP    1 337 803 B1    8/2012

OTHER PUBLICATIONS

Adrian H. Bachmann et al., "Resonant Doppler flow imaging and optical vivisection of retinal blood vessels", Jan. 22, 2007/vol. 15, No. 2/*Optics Express*, pp. 408-422.
S.H. Yun et al., "Pulsed-source and swept-source spectral-domain optical coherence tomography with reduced motion artifacts", Nov. 15, 2004/vol. 12, No. 23/*Optics Express*, pp. 5614-5624.

(Continued)

*Primary Examiner* — Mohammed Hasan
(74) *Attorney, Agent, or Firm* — Patterson Thuente Pedersen, P.A.

(57) ABSTRACT

An ophthalmological measuring system for determining distances and/or for tomographic imaging of ocular structures, based on an OCT method. The measuring system includes a light source with a spectral centroid ($\lambda$), an interferometric measuring device, a scanner system, which in addition to the lateral deflection of the sample beam also has axial modulations with a frequency (f) in the sample arm, and a control and evaluation unit. The scanner performs a lateral, two-dimensional deflection of the sample beam with the aid of one or even two separate mirror elements and can in particular have axial modulation amplitudes $z_M \gg \lambda/2$. The system can also be used for scanner systems in other fields that use an OCT method, in particular a swept-source OCT method.

17 Claims, 4 Drawing Sheets

(56) References Cited

U.S. PATENT DOCUMENTS

| | | |
|---|---|---|
| 6,654,127 B2 | 11/2003 | Everett et al. |
| 7,330,270 B2 | 2/2008 | O'Hara et al. |
| 7,336,366 B2 | 2/2008 | Choma et al. |
| 7,365,865 B2 | 4/2008 | Kidani et al. |
| 7,794,082 B2 * | 9/2010 | Bergner et al. ............... 351/205 |
| 7,929,148 B2 * | 4/2011 | Kemp ........................ 356/497 |
| 2004/0061865 A1 | 4/2004 | Drabarek |
| 2007/0291277 A1 | 12/2007 | Everett et al. |
| 2008/0165366 A1 | 7/2008 | Schmitt |
| 2008/0231808 A1 | 9/2008 | Van de Velde |
| 2009/0225324 A1 | 9/2009 | Bernstein et al. |
| 2010/0110376 A1 | 5/2010 | Everett et al. |
| 2011/0069366 A1 | 3/2011 | Antkowiak et al. |
| 2011/0255054 A1 | 10/2011 | Hacker et al. |

OTHER PUBLICATIONS

Lin An et al., "Use of a scanner to modulate spatial interferograms for in vivo full-range Fourier-domain optical coherence tomography", Dec. 1, 2007/vol. 32, No. 23/*Optics Letters*, pp. 3423-3425.

Lee, Edward C.W., et al., "In vivo optical frequency domain imaging of human retina and choroid," *Optics Express*, vol. 14, No. 10, (XP-002525498), pp. 4403-4441 (Apr. 27, 2006).

Vergnole, Sébastien, et al., "Common Path swept-source OCT Interferometer with artifact removal," *Proc. of SPIE*, vol. 6847, 68472W-1 8 pgs. Apr. 2008.

Yun, S.H., et al., "Motion artifacts in optical coherence tomography with Frequency-domain ranging," *Optics Express*, vol. 12, No. 13 (XP-002623685), pp. 2977-2998 (Jun. 21, 2004).

\* cited by examiner

OCT-BASED OPHTHALMOLOGICAL MEASURING SYSTEM

PRIORITY CLAIM

The present application is a National Phase entry of PCT Application No. PCT/EP2011/093278, filed Jul. 2, 2011, which claims priority from German Application No 10 2010 032 138.9, filed Jul. 24, 2010, the disclosures of which are hereby incorporated by reference herein in their entirety.

FIELD OF THE INVENTION

The present invention relates to an ophthalmological measuring system for determining distances and/or for tomographic imaging of ocular structures, which measuring system is based on an OCT method.

BACKGROUND

According to the prior art, methods and measuring apparatuses that are based on confocal scan systems or optical coherence tomography (OCT) have proved to be successful for determining distances and/or for tomographic imaging of ocular structures.

The great technological advantage of OCT is the decoupling of the depth resolution from the transversal resolution. In contrast to microscopy, it is possible to detect therewith the three-dimensional structure of the object to be examined. The purely reflective, and thus contactless, measurement enables generating microscopic images in vivo.

For OCT methods, coherent light is used with the aid of an interferometer for measuring distances and for imaging on reflective and scattering samples. On the human eye, due to the changes of the refractive index occurring on the optical boundary surface and due to volume scattering, the OCT methods deliver measurable signals when scanning in depth. Optical coherence tomography is a very sensitive and fast method for interferometric imaging, which is widely used in particular in the medical field and in basic research. OCT scans of ocular structures are frequently used in ophthalmology for diagnosis and therapy monitoring as well as for planning interventions and for selecting implants. An example for OCT-supported diagnosis is the use of OCT scans of the retina for determining the thickness of the retinal nerve fiber layer (RNFL) for diagnosing glaucoma and for monitoring the course of the disease.

For example, the basic principle of the OCT method described in the U.S. Pat. No. 5,321,501 is based on white light interferometry and compares the transmit time of a back-scattered sample signal (or measurement signal) with the reference signal by means of an interferometer (primarily a Michelson interferometer). Here, the arm having a known optical path length (=reference arm) is used as a reference for the measuring arm in which the sample is located. The interference of the signals from both arms forms a pattern from which the scattering amplitudes can be determined in dependence on the optical delay between the arms, and thus a depth-dependent scattering profile can be determined which, analogous to ultrasonic technology, is designated as A-scan. Rapid variations of the optical delay between measuring arm and reference arm can be implemented, for example, by means of fiber lines (EP 1 337 803 A1) or by means of so-called rapid-scanning optical delays (RSOD) (U.S. Pat. No. 6,654,127 B2). In multi-dimensional raster scans, the beam is then guided transversally in one or two directions, as a result of which a two-dimensional B-scan or a three-dimensional volume tomogram can be recorded. If the reference arm length is kept constant, a two-dimensional C-scan can be obtained during lateral scanning of the measuring beam in two directions.

Here, the arm having a known optical path length (=reference arm) is used as a reference for the measuring arm (also called sample arm). The interference of the signals from reference arm and sample arm results in an interference pattern from which the relative optical path length of scattering signals within an A-scan (depth signal) can be read out. In one-dimensional raster scans, the beam, analogous to ultrasonic technology, is then guided transversally in one or two directions, as a result of which a two-dimensional B-scan, a C-scan or a three-dimensional tomogram can be recorded. Usually, a C-scan is to be understood as a two-dimensional tomogram that has been obtained through two-dimensional scanning with a constant reference arm length in a time-domain OCT. However, this term shall be used hereinafter as a synonym for all scans that are based on two-dimensional scanning, thus also for volume scans. Here, the amplitude values of the individual A-scan are represented in linear or logarithmized grey scale values or false color values. Furthermore, it is known that through a comparison with B-scans, volume scans can be corrected with regard to inaccuracies caused by movements of the samples (U.S. Pat. No. 7,365, 865). From A. H. Bachmann et al. it is further known according to [1] that through a phase-resolved measurement, in particular through Doppler signal evaluations, additional information about dynamic processes can be obtained and represented.

Recording of A-scans is usually carried out with 400 Hz to 400 kHz, in exceptional cases even in the MHz range. Ophthalmological OCT systems have typical sensitivities of from 80 dB to 110 dB. The wavelength used depends on the targeted scanning area and the absorption and scattering behavior of the tissue. Retinal OCTs operate in most cases in the range of from 700 nm to 1100 nm, while anterior chamber OCTs preferably use long-wave radiation, for example, of 1300 nm, which is absorbed in the vitreous. However, anterior chamber OCTs can also be implemented by switching over retinal OCTs (US 2007/0291277 A1).

The axial measurement resolution of the OCT method is determined through the so-called coherence length of the light source used, which is inversely proportional to the bandwidth of the utilized radiation and is typically between 3 μm and 30 μm (short-coherence interferometry). The lateral measurement resolution is determined by the cross-section of the measuring beam in the scanning area and is between 5 μm and 100 μm, preferred below 25 μm. Due to its particular suitability for examining optically transparent media, said method is widely used in ophthalmology.

In the case of the OCT methods used in ophthalmology, two different basic types have established themselves. For determining the measured values with the first type, the length of the reference arm is changed and the intensity of the interference is continuously measured without considering the spectrum. This method is designated as "time domain" method (U.S. Pat. No. 5,321,501 A). On the contrary, in the other method, the method designated as "frequency domain", the spectrum is considered when determining the measured values, and the interference of the individual spectral components is recorded. Thus, on the one hand, this is referred to as signal in the time domain and, on the other, as signal in the frequency domain (FD-OCT).

The advantage of the "frequency domain" method is the simple and fast simultaneous measurement, wherein complete information about the depth can be determined without the need of movable parts. This increases stability and speed (U.S. Pat. No. 7,330,270 B2).

Furthermore, in the frequency domain OCT a distinction is made whether the spectral information is obtained by means of a spectrometer ("spectral domain OCT", SD-OCT) or by means of swept-source OCT (SS-OCT).

A device for swept-source optical coherence domain reflectometry by means of which an entire eye can be measured in an A-scan is described in the still unpublished specification DE 10 2008 063 225.2. For this purpose, the device comprises a tunable laser light source with a defined spectral line width and a defined sweep tuning, and at least one receiver for the light scattered back from the sample. In this manner, in particular, a low-cost and efficient distance measurement over the entire length of the eye is implemented, since, despite typical eye movements of up to 1000 µm/s and with merely moderate requirements for the sweep rate of the laser light source, disturbing signal losses due to sample displacements during the distance measurements between surfaces of the cornea and the retina can be avoided.

The great advantage of the OCT methods, as already mentioned, is the contactless measurement and the generation of microscopic images and even three-dimensional structures of the object to be examined and in particular of the tissue to be examined in vivo. A possible error source that impairs the generation of accurate measured values and topograms are movements of the sample during the measuring process. It is known from the prior art that the adverse effects of sample movements can be reduced by using swept-source OCT (SS-OCT) or pulsed spectral domain OCT (SD-OCT).

For example, it is set forth by S. H. Yun et al. in [2] that the significant movement artifacts generated by movement of the sample and/or probe during the exposure time can be considerably reduced by a short illumination of the individual CCD pixels. For this, pulsed and tunable broadband light sources are used. Through a so-called "snap shot" illumination, axial profiles of a sample with greatly reduced movement artifacts can be generated. It has been found that using pulsed or tunable broadband light sources can indeed be an alternative to the use of expensive high-speed cameras in connection with "time domain" methods.

In addition to the movement of the sample and/or the probe, the measurement results can also be negatively influenced by unintentional movements of the scanner system. In particular those movement components that vary the optical path length from the measuring system to the sample and back disturb the interferences in the measuring system and thus the measurement results. These disturbing variations of the optical path are designated hereinafter as "axial modulation" by the scanner.

While the movements of the sample and/or the probe at speeds of a few mm/s, i.e., a few Hz, are slow and can be compensated in a relatively simple manner, this does not apply to the rather high-frequency, axial modulations of the scanner system.

According to the known prior art, the occurring axial modulations of scanner systems have not been compensated up to now, but are avoided or at least minimized by the use of high-quality scanners. For this purpose, normally, single-axis scanner with little mechanical deflections perpendicular to the rotational axis (torsion modes) are used. In order to avoid "fringe washout", the recording times τ for an A-scan are reduced in known OCT systems to much less than 1/f, and/or scanner systems with axial modulation amplitudes of far below λ/2 are used. However, both variants are very cost-intensive.

An example for the use of such stable scanners is given in [4]. Here, these scanners are used for a decentered deflection of a measuring beam in order to implement very small, defined phase modulations of the optical path in the measuring arm and/or to implement Doppler shifts that allow a reconstruction of full or complex FD-OCT signals. Hereby, the usable modulations are limited due to the beginning fringe washout in the SD-OCT system used.

As particularly stable operating scanners, uniformly rotating polygon mirrors or oscillating galvanometer mirrors are used. Polygon mirrors are able to scan very fast and stable; however, they are limited to a given deflection pattern in a given direction. Moreover, they are very noisy and expensive. In contrast to that, galvanometer mirrors can implement different scan patterns, but they require very high control expenditure. Because of this, combinations of both systems are also often used as a scanner unit in ophthalmological apparatuses.

The most commonly used deflection systems in ophthalmological scanners, as described in the patent specification US 2008/231808 A1, comprise modern galvanometer scanners with an optical position detection system by means of which, via an electronic control unit, active control of the mirror movement including the damping of interferences (U.S. Pat. No. 5,999,302 A) is possible. An additional negative effect of these systems is that they are very complicated and expensive.

However, the use of simple scanner systems which, for example, can deflect the sample beams simultaneously in two directions entail the disadvantage that due to the increased number of bearings and the size of the suspensions, a sufficiently rigid design with tolerances that are much tighter than the wavelength, and thus lie in the sub-micrometer range, are extremely difficult so that minimizing occurring axial modulations is hardly possible.

Such a simple scanner system is described, for example, in the still unpublished patent specification DE 10 2009 041 995.0. The optical deflection unit is provided in particular for ophthalmological diagnosis and therapy apparatuses and comprises a deflection mirror, a position sensor and a control unit, which form a control circuit for minimizing the deviation of the actual positions detected by the position sensor from the targeted positions of the deflection mirror. A deflection mirror serves as an optical deflection unit, which deflection is movable by a contactless electromagnetic drive and oscillates about at least one rotational axis, and which, in the direction of the at least one rotational axis, is arranged between at least two bearings.

US 2009/225324 A1 describes a high-speed endoscope for optical coherence tomography that is based on a two-axis micro-mirror. Since the two-axis micro-mirror is usually moved with frequencies between 100 and 1000 Hz, accordingly, a fast OCT method is required for measured value acquisition. Used for this is a multi-function SD-OCT system that is capable of performing three-dimensional, intensity-sensitive and/or polarization-sensitive tomograms.

It is further known from the prior art that in the case of optical path length modulations of more than wavelength fractions per recorded A-scan in the OCT, major signal losses due to the so-called "fringe washout" are to be expected. S. H. Yun et al. document in [3] that the effect can go so far that in the case of optical path length variations of λ/2 per recorded scan, there is the risk of a complete signal loss because constructive and destructive interferences possibly average each other out.

Literature:

[1] A. H. Bachmann, M. L. Villiger, C. Blatter, T. Lasser and R. A. Leitgeb, "Resonant Doppler flow imaging and optical vivisection of retinal blood vessels", Vol. 15, No. 2/ OPTICS EXPRESS 408.

[2] S. H. Yun, G. J. Teamey, J. F. de Boer, and B. E. Bouma, "Pulsed-source and swept-source spectral-domain optical coherence tomography with reduced motion artifacts", Vol. 12, No 23/ OPTICS EXPRESS 5614.

[3] S. H. Yun, G. J. de Boer, and B. E. Bouma, "Motion artifacts in optical coherence tomography with frequency-domain ranging", Vol. 12, No. 13/OPTICS EXPRESS 2980.

[4] Lin An and Ruikang K. Wang, "Use of a scanner to modulate spatial interferograms for in vivo full-range Fourier-domain optical coherence tomography", Vol. 32, No. 23/ OPTICS LETTERS.

SUMMARY OF THE INVENTION

It is an object of the present invention to develop an OCT-based ophthalmological measuring system in which the influence of occurring axial modulations of the scan system is compensated or at least minimized.

This object is achieved with the OCT-based ophthalmological measuring system, comprising a light source with a spectral centroid λ, an interferometric measuring arrangement, a scanner system which, in addition to the lateral deflection of the sample beam, also causes axial modulations with a frequency f in the sample arm, and a control and evaluation unit, in that the measuring system is a swept-source OCT system and the sweep time dλ/dt of the tunable light source is adapted to the desired maximum measuring depth z and the frequency f of the axial modulation of the scanner system.

According to the invention, the object is achieved by the features described herein. Preferred refinements and configurations are also discussed herein.

A particularly advantageous example configuration is achieved if the amplitude $z_M$ of the axial modulation of the scanner system is smaller than the resolution δz of the swept-source OCT systems. Here, the sweep times dλ/dt of the light source itself during axial modulations with frequencies f between 100 Hz and 10,000 Hz can be approximately at least $\lambda^2*f/(4z)$ and in particular also more than $\lambda^2*f/z$. For adapting the sweep times of the light source to expected modulation frequencies, the latter can also be determined by analyzing mechanical resonances by means of computer simulation, for example by means of FEM (finite element method).

The use of the proposed OCT-based measuring system is intended in particular for the area of ophthalmology and there for determining distances and/or for tomographic imaging of ocular structures.

In particular in this area, the solution offers the possibility of using inexpensive scanner systems, as a result of which the construction of the overall apparatus is greatly simplified.

However, the proposed measuring system is also applicable to scanner systems in other areas which can use an OCT method, in particular a swept-source OCT method.

BRIEF DESCRIPTION OF THE DRAWINGS

The invention is described in more detail hereinafter by means of exemplary embodiments. For a better illustration of the inventive solution.

FIG. 1 depicts the use of a scanner system with an amplitude $z_M$ of the axial modulation with $z_M > \lambda/10$, in particular $z_M = \pm 2$ μm, FIG. 2 depicts the use of scanner system with an amplitude $z_M$ of the axial modulation with $z_M \gg \lambda/2$, in particular $z_M = \pm 10$ μm, FIG. 3 depicts the use of an ophthalmological measuring system according to the prior art with an amplitude $z_M$ of the axial modulation with $z_M > \lambda/2$, in particular $z_M = \pm 10$ μm.

DETAILED DESCRIPTION

Figure 1:
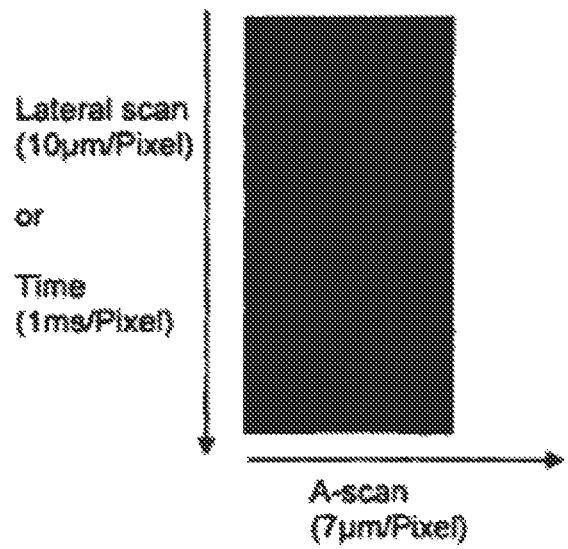
FIGS. 1-3 show B-scans of a glass plate.

The OCT-based ophthalmological measuring system according to the invention comprises a light source with a spectral centroid λ, an interferometric measuring arrangement 2, a scanner system 3 which, in addition the lateral deflection 4 of the sample beam, also causes axial modulations with a frequency f in the sample 7 arm, and a control and evaluation unit 8. Here, a scanner system 3 is to be understood as systems which perform a lateral two-dimensional deflection of the sample beam with the aid of one or even two separate mirror elements 4, and which in particular can have axial modulation amplitudes $z_M \gg \lambda/2$.

As a measuring system, a swept-source OCT system is used here. The sweep time dλ/dt of the tunable light source is adapted to the targeted maximum measuring depth z 13 and the frequency f of the axial modulation of the scanner system 3.

The targeted maximum measuring depth z 13 is determined in ophthalmology by the length of the eyes to be measured, which length typically varies between approx. 20 and 32 mm (in extreme cases between 14 and 40 mm), wherein the refractive indices of the eye media are also to be considered. If an average refractive index of 1.36 is specified and an adjustment range of 5 mm in air, the result is a required optical measuring depth of approx. 60 mm.

Thus, the "residence time" of the measuring system during the individual modulations of the interference signal remains small with respect to the mechanical modulation frequencies f of the scanner system. The effects of the "fringe washout" thus can be avoided, although the total recording time for an A-scan can be significantly greater than 1/f.

For the area of ophthalmology it is of advantage that the spectral centroid λ of the light source lies in a range of from 700 nm to 900 nm, and is in particular 800 nm, and/or in a range of from 1000 nm to 1100 nm, and is in particular 1060 nm. Here, the light source for example has a bandwidth Δλ of 3 nm to 100 nm at the spectral centroid λ.

Due to the use of a swept-source OCT system as an ophthalmological measuring system and the adaptation of the sweep time dλ/dt of the light source 1 to the measuring depth z 13 and the frequency f of the axial modulation of the scanner system, scanner systems can be used, the axial modulation amplitude $z_M$ of which can be considerably more than only fractions of the wavelength λ. In particular, the amplitude $z_M$ of the axial modulation of the scanner system during the sweep time dλ/dt can be more than λ/10 to λ/2, even more than 1 μm.

In a particularly advantageous configuration of the ophthalmological measuring system according to the invention, the amplitude $z_M$ of the axial modulation of the scanner system is smaller than the resolution δz of the swept-source OCT system, which can be determined according to the following equation:

$$\delta z = 2*\ln(2)*\lambda^2/(\Delta\lambda*\pi) \quad (1)$$

wherein Δλ corresponds to the bandwidth of the light source. Here, the axial modulations do not result in a decrease of the axial resolution δz of the swept-source OCT system.

However, measurements are principally also possible with the solution according to the invention if the amplitude $z_M$ of the axial modulation of the scanner system is greater than the resolution δz of the swept-source OCT system. The sweep time dλ/dt of the light source, which sweep time is adapted to the targeted maximum measuring depth z and the frequency f of an axial modulation of the scanner system, is at least $d\lambda/dt=\lambda^2*f/4z$ and is in particular also more than $d\lambda/dt=\lambda^2*f/z$, even at frequencies f of the axial modulation between 100 Hz . . . 10,000 Hz. This condition can also be fulfilled for a plurality of frequencies if a plurality of axial modulations are superimposed.

Figure 2:
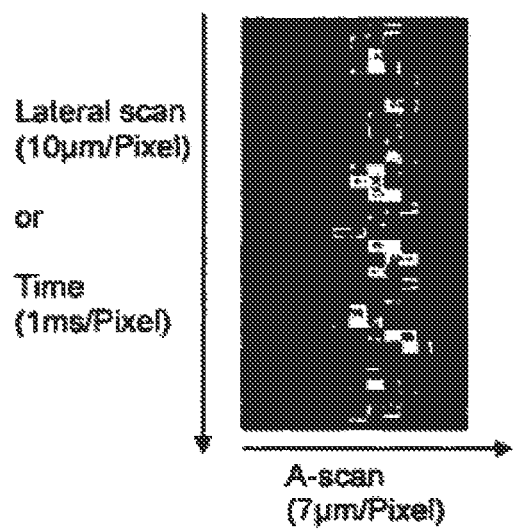
Figure 3:
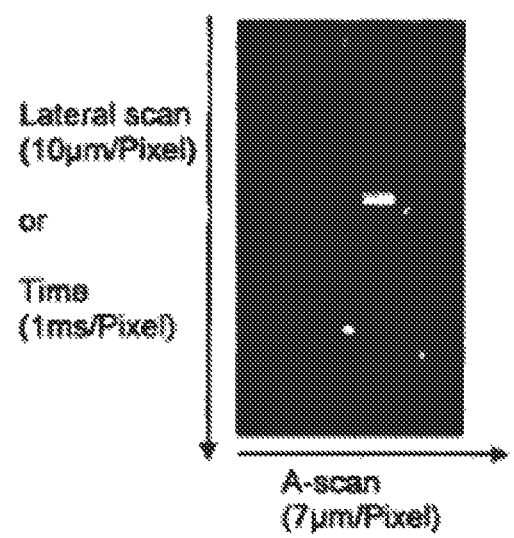
Figure 4:
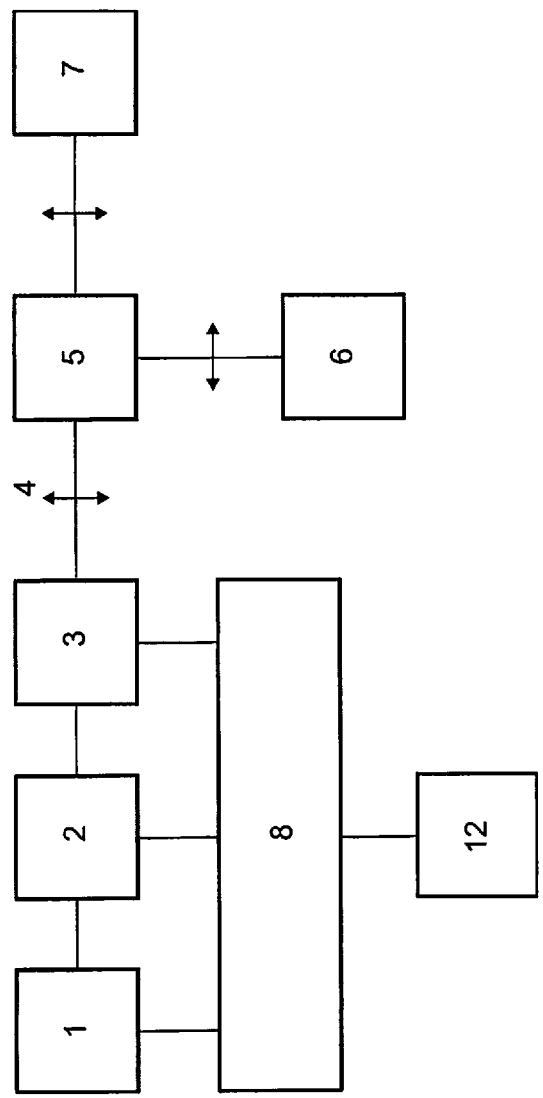
FIG. 4 is a schematic depiction of a OCT based ophthalmological measuring system according to an example embodiment of the invention.
Figure 5:
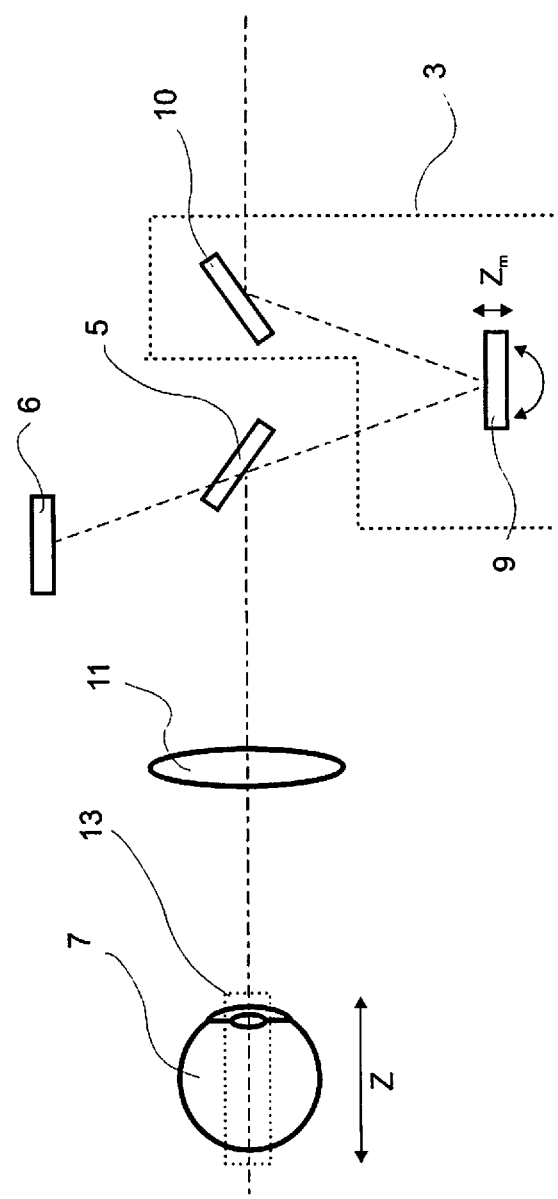
FIG. 5 is a more detailed schematic depiction of a OCT based ophthalmological measuring system according to an example embodiment of the invention.

Concerning this, the FIGS. 1 to 3 show B-scans of a glass plate. Since the thickness of the glass plate and the maximum measuring depth of z=10 mm are greater here than the illustrated region, only sections of the B-scans with a boundary surface are illustrated.

Said B-scans were recorded by using a swept-source OCT system (SS-OCT), a tunable light source with a spectral centroid λ=1 μm and a sweep time dλ/dt=30 nm/ms, and a scanner system with a modulation amplitude $z_M$ of more than λ/10.

With a resolution of the swept-source OCT system of δz=7 μm/pixel, the lateral scan speed was 10 μm/pixel or 1 ms/pixel.

The B-scans illustrated in FIG. 1 were recorded by using a scanner system with a modulation frequency f of from 200 Hz to 2000 Hz and a modulation amplitude of $z_M=\pm2$ μm. The uniform intensity of the signal curve in FIG. 1 shows that neither the amplitude $z_M$ nor the frequency f of the axial modulation of the scanner system could have influenced the signal acquisition in the ophthalmological measuring system according to the invention. There is also no sign of a decrease of the axial resolution of the SS-OCT system as a result of the axial modulations of the scanner system.

In contrast to this, FIG. 2 shows B-scans which were also recorded using a scanner system with a modulation frequency f of 200 Hz to 2000 Hz; however, the modulation amplitude thereof is $z_M=\pm10$ μm.

As the signal curve in FIG. 2 shows, measurements are principally also possible if the modulation amplitude $z_M$ of the scanner is greater than the resolution δz of the swept-source OCT system. This results in shifted boundary surface signals in the B-scan and thus in an irregular signal curve. However, a so-called "fringe washout" or even a complete signal loss as in the prior art does not occur.

Although an influence on the measurement results due to shifting is to be expected in the case of relatively great modulation amplitudes $z_M$ of the scanner system, in particular if they are greater than the resolution δz of the swept-source OCT system, it can nonetheless be ensured with the solution according to the invention that with regard to the intensity, a continuous signal curve can be recorded.

In a particularly advantageous variant, the OCT-based ophthalmological measuring system has an additional known reference structure 6. The interferometric measuring arrangement is designed here such that reference structure 6 signals of the additional known reference structure 6 and measurement signals of the eye 7 can be generated simultaneously, and the control and evaluation unit is able to evaluate the interferences of the reference structure 6 signals caused by the axial modulations of the scanner system and to utilize this for correcting the measurement signals of the eye 7. The reference structure 6 has at least one boundary surface and is preferably a planar glass plate.

The reference structure 6 signals generated on the (planar) boundary surface directly reflect the interferences caused by the axial modulations of the scanner system 3. The correction of the measurement signals of the eye 7 thus can be carried out through simple (identical) shifts. Hereby, even shifts by fractions of a pixel can be carried out by interpolation.

In a first configuration hereto, the reference structure 6 is arranged before the eye. Thus, the reference structure 6 is "measured at the same time" in a simple manner in that the boundary surface of the planar glass plate serving as a reference structure 6 reflects a portion of the measuring beam as a reference structure 6 signal. Generating the structure 6 signals is carried out here before and/or behind the eye, i.e., on the forward and/or return path of the measuring light.

In a second configuration, the OCT-based ophthalmological measuring system has an element for decoupling 5 a portion of the measuring beam so that reference structure 6 signals of an additionally present known reference structure 6 and measurement signals of the eye can be generated simultaneously by the interferometric measuring arrangement. Here, the control and evaluation unit 8 is able to evaluate the interferences caused by the axial modulation of the scanner system 3 and to utilize this for correcting the measurement signals of the eye 7.

Preferably, the element for decoupling 5 a portion of the measuring beam is arranged downstream of the scanner system 3. In this manner it is ensured through a suitable configuration and/or illumination of the structure of the reference structure that reproducible reference structure signals can be obtained.

Thereby it is possible to further reduce the influence of the axial modulations of the scanner system 3 on the measurement results. For this purpose, a portion of the measuring beam is used to simultaneously measure next to the sample the reference structure 6 that has a known form. From the obtained reference structure signals, the control and evaluation unit 8 determines form deviations of the reference structure 6 and utilizes this for correcting the measurement signals of the eye 7.

The schematic illustration shown in FIG. 3 serves for a better visualization of the advantages of the inventive solution by showing a possible signal curve when recording B-scans of a glass plate according to the FIGS. 1 and 2; however, a measuring system known from the prior art, such as a non-pulsed SD-OCT, is used here.

As already explained and shown in FIG. 3, optical path length modulations of the scanner system of more than fractions of a wavelength can result in a so-called "fringe washout" or even in a complete signal loss (dark signal drop-out areas) in the OCT.

In a particularly advantageous configuration, a simple scanner system having only one deflection mirror 9 is used for the proposed OCT-based measuring system. Such a simple scanner system is described, for example, in the still unpublished patent specification DE 10 2009 041 995.0. Here, a movable deflection mirror 9 oscillating about one, but preferably two, rotational axes serves as an optical deflection unit.

With the ophthalmological measuring system according to the invention, a solution is made available by means of which the influence of occurring axial modulations of the scan system 3 during the determination of distances and/or the tomographic imaging of ocular structures based on an OCT method is compensated or at least minimized.

This has been achieved by the use of a swept-source OCT system as a measuring system in connection with a tunable light source, wherein the sweep time $d\lambda/dt$ of the light source is adapted to the maximum measuring depth z 13 as well as to the modulation frequency f of the scanner system.

From the prior art, up to now, no solutions are known in which scanner systems with great axial modulations which, in particular, can lie in the micrometer range are employed successfully.

The proposed technical solution is in particular interesting for scanner systems which deflect the sample beams 4 in two directions at the same time. In these systems in the form of only one mirror element, to be more specific, a sufficiently rigid design for axial modulations, in particular of more than only fractions of a wavelength or in the sub-micrometer range, is extremely difficult due to the increased number of bearings and the size of the suspension.

With the proposed solution it is possible to implement scanners, in particular for OCT systems, in a significantly more cost-effective manner if, in addition to the angular deflection to be performed, axial path length modulations of significantly more than only fractions of the wavelength are also allowed.

1. tunable light source
2. interferometric measurement arrangement
3. scanner system
4. deflection of sample beam
5. coupling element, split mirror
6. reference structure
7. sample (eye)
8. control and evaluation unit
9. deflection mirror with axial motion component of amplitude $Z_m$ and frequency f
10. bending mirror
11. scan optic
12. display for displaying measurement of depth Z
13. measurement range of depth Z

The invention claimed is:

1. An OCT-based ophthalmological measuring system, comprising:
   a tunable light source emitting light with a spectral centroid $\lambda$;
   an interferometric measuring arrangement;
   a scanner system which, in addition to lateral deflection of a sample beam, also causes axial modulations with a frequency f in a sample arm; and
   a control and evaluation unit;
   wherein the measuring system comprises a swept-source OCT system and a tuning speed $d\lambda/dt$ of the tunable light source is adapted to the maximum measuring depth z and a frequency f of the axial modulation of the scanner system.

2. The OCT-based ophthalmological measuring system according to claim 1, wherein the spectral centroid $\lambda$ of the light source lies in a range of from 700 nm to 900 nm.

3. The OCT-based ophthalmological measuring system according to claim 2, wherein the spectral centroid $\lambda$ of the light source is 800 nm.

4. The OCT-based ophthalmological measuring system according to claim 1, wherein the spectral centroid $\lambda$ of the light source lies in a range of from 1000 nm to 1100 nm.

5. The OCT-based ophthalmological measuring system according to claim 4, wherein the spectral centroid $\lambda$ of the light source is 1060nm.

6. The OCT-based ophthalmological measuring system according to claim 1, wherein the light source has, at the spectral centroid $\lambda$, a bandwidth $\Delta\lambda$, of 3 nm to 100 nm.

7. The OCT-based ophthalmological measuring system according to claim 1, wherein an amplitude $z_M$ of the axial modulation of the scanner system during the tuning speed $d\lambda/dt$ is more than $\lambda/10$ to $\lambda/2$.

8. The OCT-based ophthalmological measuring system according to claim 1, wherein an amplitude $z_M$ of the axial modulation of the scanner system during the tuning speed $d\lambda/dt$ is more than 1 µm.

9. The OCT-based ophthalmological measuring system according to claim 1, wherein an amplitude $z_M$ of the axial modulation of the scanner system is smaller than the resolution $\delta z$ of the swept-source OCT system, and $$\delta z = 2*\ln(2)*\lambda^2/(\Delta\lambda*\pi)$$

wherein $\Delta\lambda$ corresponds to the bandwidth of the light source.

10. The OCT-based ophthalmological measuring system according to claim 1, wherein, in the case of expected axial modulations with frequencies f between 100 Hz and 10,000 Hz, the tuning speed $d\lambda/dt$ of the light source is at least $\lambda^2*f/(4z)$.

11. The OCT-based ophthalmological measuring system according to claim 1, wherein, in the case of expected axial modulations with frequencies f between 100 Hz and 10,000 Hz, the tuning speed $d\lambda/dt$ of the light source is more than $\lambda^2*f/z$.

12. The OCT-based ophthalmological measuring system according to claim 1, further comprising:
    an additional known reference structure; and
    wherein the interferometric measuring arrangement is designed such that reference structure signals of the additional known reference structure and measurement signals of the eye can be generated simultaneously, and the control and evaluation unit is programmed to evaluate interference of the reference structure signals, which interferences are caused by the axial modulations of the scanner system, and to utilize results of the evaluation of the interference of the additional known reference structure signals to correct the measurement signals of the eye.

13. The OCT-based ophthalmological measuring system according to claim 12, wherein the additional known reference structure has at least one boundary surface.

14. The OCT-based ophthalmological measuring system according to claim 12, wherein the additional known reference structure is a planar glass plate.

15. The OCT-based ophthalmological measuring system according to claim 12, wherein the additional known reference structure is arranged before the eye.

16. The OCT-based ophthalmological measuring system according to claim 12, further comprising an element that decouples a portion of the measuring beam such that reference structure signals of the additional known reference structure and measurement signals of the eye are simultaneously generated by the interferometric measuring arrangement; and
    wherein the control and evaluation unit is programmed to evaluate the interferences of the reference structure signals, which interferences are caused by the axial modulations of the scanner system, and to utilize results of the evaluation to correct the measurement signals of the eye.

17. The OCT-based ophthalmological measuring system according to claim 16, that the element that decouples a portion of the measuring beam is arranged downstream of the scanner system.

* * * * *

UNITED STATES PATENT AND TRADEMARK OFFICE
CERTIFICATE OF CORRECTION

| | | |
|---|---|---|
| PATENT NO. | : 8,845,097 B2 | Page 1 of 1 |
| APPLICATION NO. | : 13/812113 | |
| DATED | : September 30, 2014 | |
| INVENTOR(S) | : Martin Hacker et al. | |

It is certified that error appears in the above-identified patent and that said Letters Patent is hereby corrected as shown below:

In the claims

Col. 9, line 44, delete "fin" and insert --f in--

Signed and Sealed this
Second Day of February, 2016

Michelle K. Lee
*Director of the United States Patent and Trademark Office*